(12) United States Patent
Powell

(10) Patent No.: US 6,238,375 B1
(45) Date of Patent: May 29, 2001

(54) RETRACTABLE COVER EXTRACTION FOR INTRAVENOUS AND OTHER THERAPY NEEDLES

(76) Inventor: Richard R. Powell, 3139 Diamond Knot Cir., Tampa, FL (US) 33607

( * ) Notice: Subject to any disclaimer, the term of this patent is extended or adjusted under 35 U.S.C. 154(b) by 0 days.

(21) Appl. No.: 08/582,201

(22) Filed: Jan. 2, 1996

(51) Int. Cl.[7] ..................................................... A61M 5/00
(52) U.S. Cl. ........................................... 604/263; 128/919
(58) Field of Search ............................ 604/115–117, 110, 604/93, 171, 192, 198, 263, 289, 290, 310, 311; 606/1; 128/919; 206/363, 364, 365, 367

(56) References Cited

U.S. PATENT DOCUMENTS

| | | | |
|---|---|---|---|
| 4,897,083 | * | 1/1990 | Martell .................................. 604/263 |
| 5,061,246 | * | 10/1991 | Anapliotis ............................. 604/171 |
| 5,295,975 | * | 3/1994 | Lockwood, Jr. ...................... 604/263 |
| 5,476,452 | * | 12/1995 | Thompson ............................ 128/919 |

* cited by examiner

*Primary Examiner*—Ronald K. Stright, Jr.
(74) *Attorney, Agent, or Firm*—Dennis G. LaPointe; Mason & Associates, PA

(57) ABSTRACT

A retractable multi-piece cover for use in removal of a needle delivery system over a central venous access port which is subcutaneously implanted into a patient. The multi-piece cover extends to surround the intravenous therapy needle during its removal from the port so that the person removing the needle is protected from the possibilities of spattering blood and needle stick resulting from needle rebound. The multi-piece cover may have an upper slit in its extendable upper portion, or a larger opening in its extendable upper portion covered with flexible material through which an intravenous therapy needle may access the port. The multi-piece cover may also have a clamp for securely attaching the multi-piece cover to the intravenous therapy needle. Applications may include, but are not limited to, use over subcutaneously arm-implanted ports and subcutaneously chest-implanted ports.

13 Claims, 5 Drawing Sheets

RETRACTABLE COVER EXTRACTION FOR INTRAVENOUS AND OTHER THERAPY NEEDLES

BACKGROUND

1. Field of Invention

This invention relates to but is not him limited shielding devices, specifically to a retractable multi-piece cover for use over a subcutaneously implanted port which extends during removal of a needle from the port so as to surround the needle as it is withdrawn from the patent so that the person removing the needle is protected from spattering blood and possible needle stick resulting from needle rebound. Applications may include, but are not limited to, use over subcutaneously arm-implanted ports and subcutaneously chest-implanted ports, and other indewelling needle systems used in clinical settings.

2. Description of Prior Art

Historically, long-term therapy treatments involving the intravenous administration of medications have presented patents with a variety of apprehensions and problems. Even when treatment was lengthy, or repeated often, delivery of the medications occurred through repeated injections into the small veins of the patient, such as those in the patient's arm. Repeated needle punctures into the patient's veins often caused pain, as well as injury to the patient's veins. Also, some medications themselves were known to injure the small veins. Additional needle punctures, resulting from the withdrawal of blood from the patient, were also needed to monitor the effect of the medication on the patient. Anxiety in patients prior to therapy treatments was common.

Catheters were developed for the direct administration of medications into a patient through the large vein near the patient's heart. Such direct administration allows for faster circulation of medication within the patient's system, and prevents injury to small veins which repeated needle punctures and concentrated medications may cause. Two types of catheters have been developed for use in central venous therapy. One is the external catheter which has a small piece of flexible tubing with a connector on one of its ends. Part of the tubing and the connector remain outside of the patient's body. The other end of the tubing is placed into the large vein near the heart. The external catheter is commonly placed into the patient's arm or the patient's chest and may be covered with a sterile covering between therapy treatments. After the external catheter is installed through the patient's skin, a syringe or other delivery device is used for infusing medication into the patent through the external connector. Disadvantages of external catheters is that maintenance is required to minimize infection around the opening in the patent's skin through which the catheter protrudes. Also, periodic flushing is required to keep external catheters open and the patent's activity may be restricted.

The other type of catheter for central venous access is surgically positioned within a patient, between the large vein near the heart and a subcutaneously implanted port. No part of the second type of central venous access protrudes through the skin of the patient. The subcutaneously implanted ports are commonly chest-placed, or arm-placed, so as to minimally restrict a patient's activity. The ports also have a self-sealing septum through which a needle may be inserted for delivery of medications. Blood samples may also be withdrawn through such ports. A needle may remain in a septum for a period of time to allow for an optimum flow-rate of medication into the patient. Ports usually involve little or no activity restriction and minimal maintenance. Further, the small hump made by a port under the patent's skin is less noticeable than a connector attached to a protruding piece of tubing. One problem associated with such ports develops upon removal of the needle from the port. When pressure is exerted on the angled needle to remove it from the port, frictional resistance may cause the needle to temporarily bind against the septum, requiring the person removing it to exert additional force to withdraw the needle. When the needle finally releases from the septum, a downward needle rebound develops which may cause the needle to penetrate the skin of the person withdrawing the needle, or the skin of the patient. The present invention eliminates the problems associated with needle rebound and also protects the person removing the needle from patient's blood which may spatter during removal of the needle from these instances and other healthcare giver needle use situations involving many types of systems.

The prior art known to be most closely related to the present invention are the inventions disclosed in U.S. Pat. No. 5,187,815 to Medev Corporation (1993) and U.S. Pat. No. 5,342,311 to Darina (1994). The Medev Corporation invention discloses a needlestick protective glove which would protect the fingers of a person removing a medication delivery needle from a subcutaneously implanted port. The Darina skin shield invention discloses a flexible annular disc having finger tabs and a central disc opening. The disc is thick enough to resist needle penetration. The finger tabs help a person removing a needle from a subcutaneously implanted port to apply pressure to the site of the implanted port for site stabilization so that the disc will help to protect the persons fingers from accidental needle stick during needle rebound. In contrast to the Medev Corporation and the Darina inventions, the present invention extends upon needle removal to surround the area above the port, through which the needle travels during its removal from the port, to prevent accidental needle penetration into the person removing it, or into the patient during needle rebound. Many healthcare workers who wear gloves often and develop sensitive skin from repeatedly wearing gloves would prefer to use the present invention instead of the Medev Corporation invention. Also, since the present invention completely needle tip surrounds a after it is removed from the patent, the present invention would protect the person removing it from accidental needle stick resulting from needle rebound better than a disc which merely covers the port site.

SUMMARY OF INVENTION —OBJECTS AND ADVANTAGES

It is the primary object of this invention to provide a cover for a subcutaneously implanted intravenous therapy port needle infusion delivery system which completely surrounds the needle after its removal from the port septum so that the person removing the needle and the patent are both protected from needle stick resulting from needle rebound. It is a secondary object of this invention to provide a cover for a subcutaneously implanted intravenous therapy port needle infusion delivery system which covers the area through which the needle travels during its removal from the port septum so as to protect the person removing the needle from spattering blood. A further object of this invention is to provide a multi-piece cover for a subcutaneously implanted intravenous therapy port needle infusion delivery system which expands to cover the area through which the needle travels during its removal from the port septum. It is also an object of this invention to provide a cover for a subcutaneously implanted intravenous therapy port needle infusion delivery system which has a needle guard which closes over the needle as it is removed from the port site so that the person removing a needle from the port site and the patient are both protected from needle stick resulting from needle rebound.

As described herein, properly manufactured and installed over a subcutaneously implanted port needle infusion delivery system, the present invention would provide a multi-piece cover for enclosing a medication delivery needle upon its removal from the port septum to protect both the person removing the needle and the patient from needle penetration resulting from needle rebound. A secondary advantage of the present invention is that it would provide a cover for the area above a subcutaneously implanted port, infusion delivery system so that a person withdrawing a needle from the port is protected from spattering blood. Concurrent with needle withdrawal, the top portion of the cover would slidedly extend upward from its initial collaped position in the bottom portion so that together the top portion and the bottom portion fully surround the needle after removal. Once the needle is pulled from the port septum and the skin of the patient, the needle guard automatically moves to close over the bottom opening in the cover so that the needle is not able to penetrate into the person removing it, or into the patent, during needle rebound. In one embodiment of the present invention, the needle guard is spring biased to close against the opening in the bottom portion of the cover. In the second embodiment of the present invention, the needle guard is supported between inner and outer cover members so that the needle guard is allowed to collapse into place over the bottom opening in the outer cover member, acting as a collapsible cobling plastic as the inner cover member extends upwardly with the withdrawing needle.

The description herein provides preferred embodiments of the present invention but should not be construed as limiting the scope of the port cover invention. Variations in extended height of the retractable cover, the space within the cover which laterally surrounds the needle, the material from which the cover is made, the type of means used to bias the cover into an extended position, the type of hinge used to position the needle guard over the tip of a needle withdrawn from the port, and the means by which the needle guard moves into position to protect the person removing the needle from needle stick resulting from needle rebound, other than those shown and described herein, can be incorporated into the present invention. Thus the scope of the present invention should be determined by the appended claims and their legal equivalents, rather than the examples given.

DETAILED DESCRIPTION OF PREFERRED EMBODIMENTS

Figure 1:
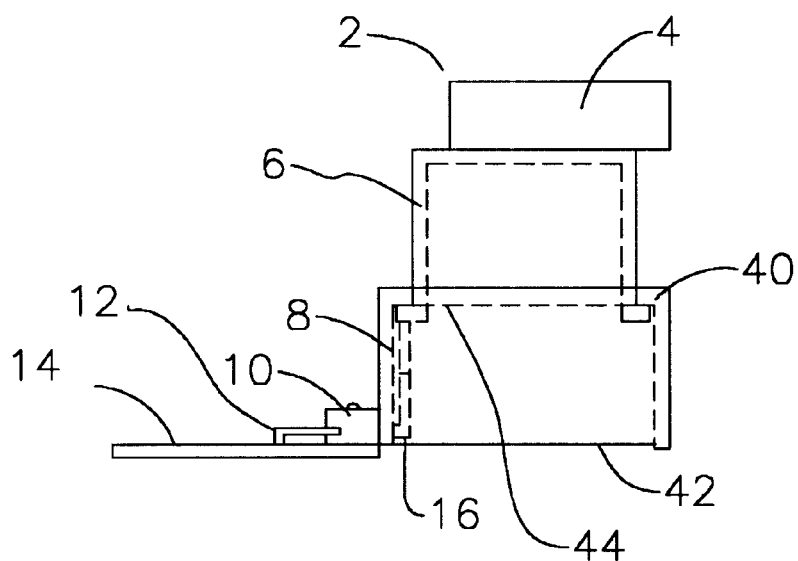
FIG. 1 is a side view of the first embodiment of the invention having a bottom cover, a top cover extending from the bottom cover, and a needle guard attached to or part of the bottom cover, the needle guard being in an opened position.

FIG. 1 shows a first embodiment of a retractable needle cover invention 2 having a bottom cover 8, a top cover 6 extendable upward from bottom cover 8, and a needle guard 14 attached to bottom cover 8 with a hinge 10. Bottom cover 8 has a central opening through its top surface through which top cover 6 may protrude in its extended position. Stopping means 40 prevent top cover 6 from moving upward beyond the central top surface opening in bottom cover 8. Bottom cover 8 also has a bottom opening 42 through which an intravenous therapy needle 18, shown in FIG. 2, may access a subcutaneously implanted port (not shown). Top cover has a slit 26 in its upper surface through which intravenous therapy needle 18 may be inserted. Top cover 6 also has a lower opening 44 through which intravenous therapy needle 18 may pass. A top cover spring 16, attached between top cover 6 and bottom cover 8 minimally biases top cover 6 into an extended position. A needle guard spring 12, attached between hinge 10 and needle guard 14, minimally biases needle guard 14 into a closed position over the bottom opening in bottom cover 8. FIG. 1 also show needle cover invention 2 having a needle clamp 4 for securing intravenous therapy needle 18 to needle cover invention 2 during use. It is contemplated for top cover 6, bottom cover 8, and needle guard 14 to be made of puncture-resistant material. In the preferred embodiment, top cover 6, bottom cover 8 and needle guard 14 are made of plastic so that needle cover invention 2 may be disposable.

Figure 2:
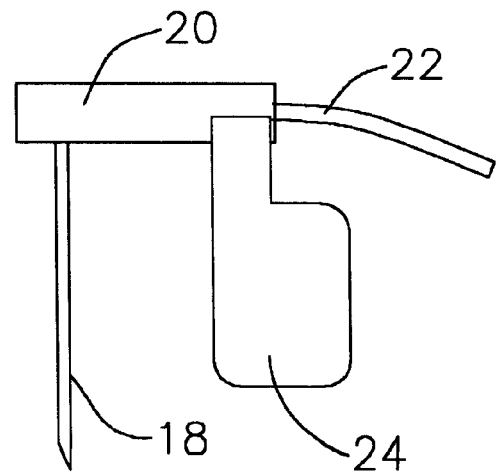
FIG. 2 is a side view of an intravenous therapy needle around which the present invention may be positioned

FIG. 2 shows intravenous therapy needle 18 attached to a needle support 20. Adhesive pads 24 attached to needle support 20 secure intravenous therapy needle 18 to a patient (not shown) during use, thereby maintaining the top and bottom covers in a collapsed position while the needle is inserted into the patient. FIG. 2 also shows a tube 22 attached through needle support 20 to intravenous therapy needle 18 for the delivery of medication (not shown) to intravenous therapy needle 18. It is also customary for healthcare givers to use a tape over any intravenous therapy needle inserted into a patient to ensure the patient does not inadvertently pull the needle out thereby further ensuring that the top and bottom covers remain in a collapsed position while the needle is inserted into the patient.

Figure 3:
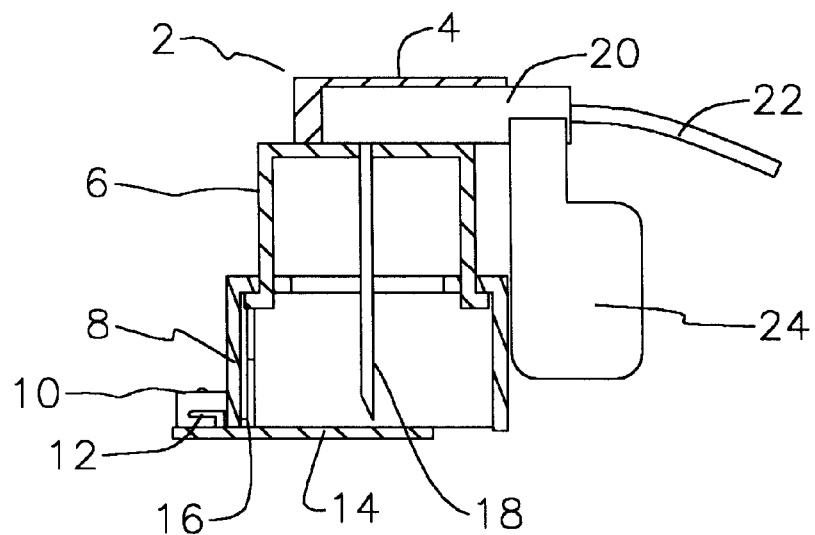
FIG. 3 is a side view of the first embodiment showing the present invention surrounding an intravenous therapy needle with the needle guard in a closed position over the lower opening in the bottom cover.
Figure 4:
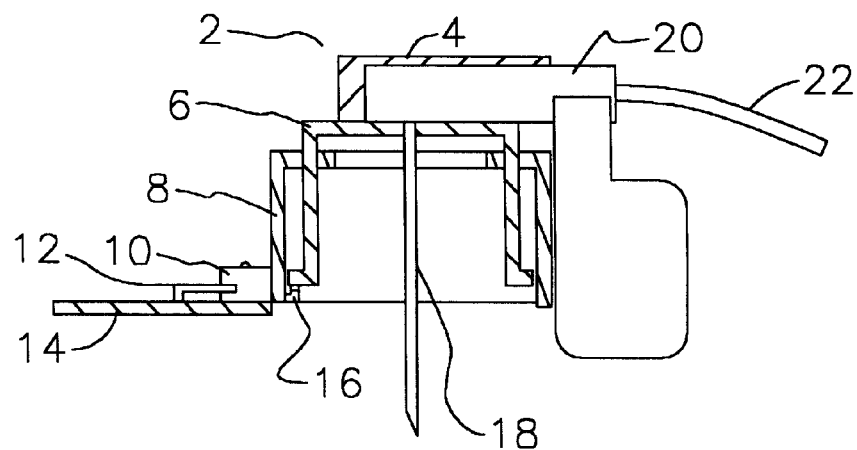
FIG. 4 is a side view of the first embodiment showing the present invention surrounding an intravenous therapy needle with the needle guard in an opened position.

FIGS. 3 and 4 show the first embodiment of needle cover invention 2 with needle support 20 attached to needle clamp 4 and intravenous therapy needle 18 supported completely within a space defined by top cover 6 and bottom cover 8. In FIG. 3 needle guard 14 is closed against bottom cover 8 and top cover 6 is extended upward and away from bottom cover 8. In FIG. 4 needle guard 14 is in an opened position and top cover 6 is retracted so that intravenous therapy needle 18 may be inserted into a subcutaneously implanted port (not shown) which is positioned beneath needle cover invention 2.

Figure 5:
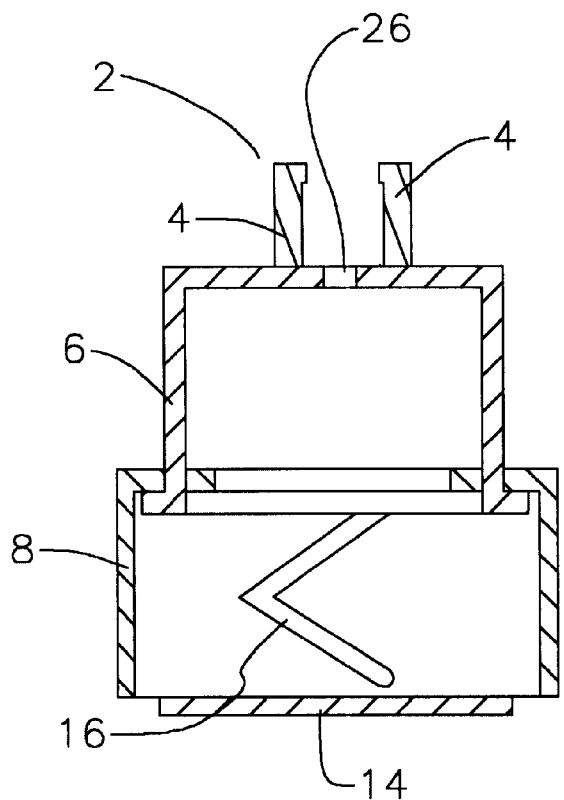
FIG. 5 is a back view of the first embodiment showing the present invention having the needle guard in a closed position and also having a slit through upper surface of the top cover for insertion therethrough of an intravenous therapy needle.
Figure 6:
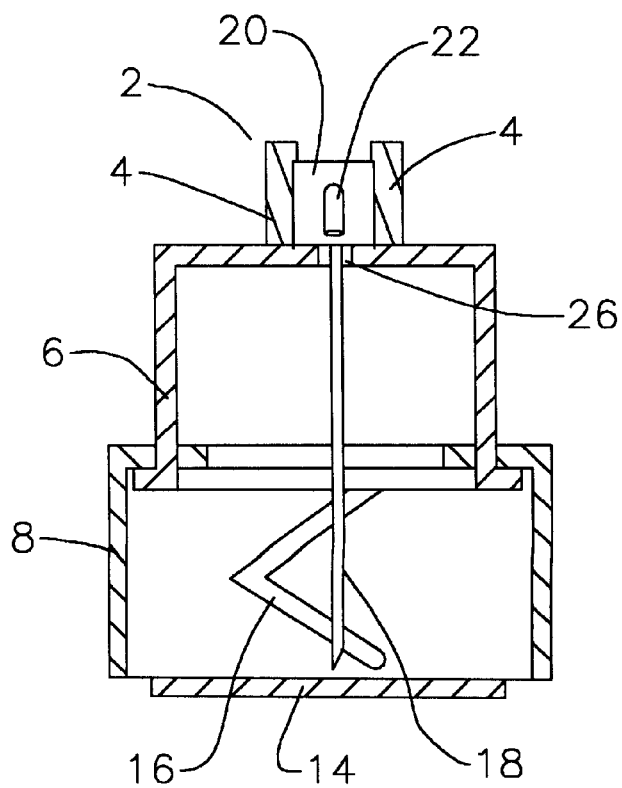
FIG. 6 is a back view of the first embodiment showing the present invention surrounding an intravenous therapy needle with the needle guard in a closed position over the lower opening in the bottom cover.

FIG. 5 shows the first embodiment of needle cover invention 2 with top cover spring 16 biasing top cover 6 into its extended position, ready for attachment of intravenous therapy needle 18. FIG. 6 shows intravenous therapy needle 18 supported within the first embodiment of needle cover invention 2 and needle guard 14 in a closed position across the lower opening in bottom cover 8.

Figure 7:
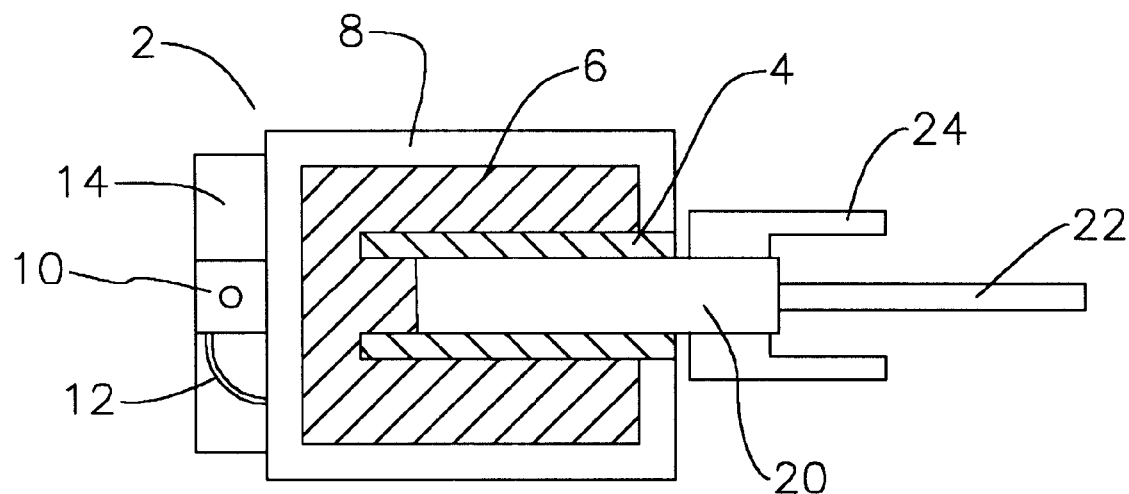
FIG. 7 is a top view of the first embodiment of the present invention surrounding an intravenous therapy needle with the needle guard in a closed position over the lower opening in the bottom cover.
Figure 8:
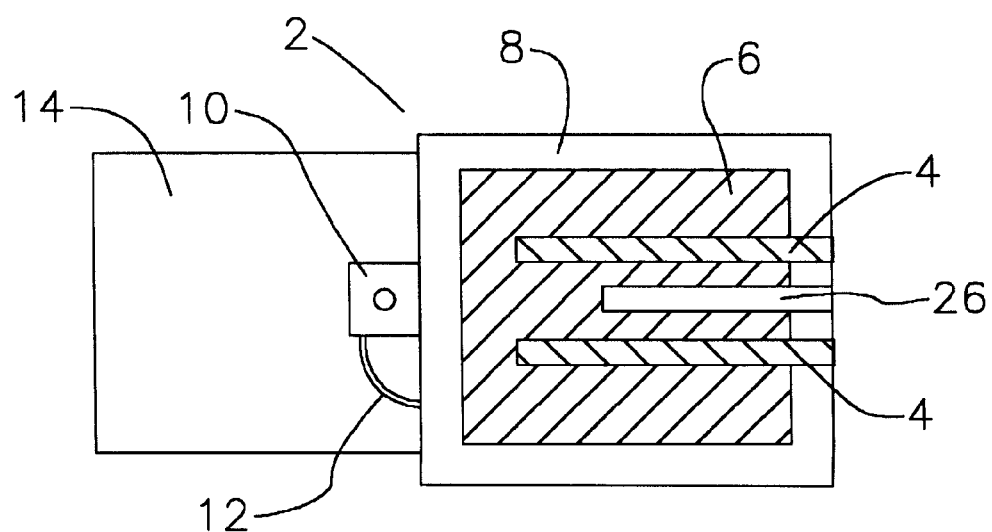
FIG. 8 is a top view of the first embodiment showing the present invention having the needle guard in an opened position and also having a slit through the upper surface of the top cover for insertion therethrough of an intravenous therapy needle.

FIG. 7 shows needle support 20 attached to the first embodiment of needle cover invention 2 with needle guard 14 in a closed position across the lower opening in bottom cover 8. FIG. 8 shows the first embodiment of needle cover invention 2 having slit 26 or other needle accepting aperture therethrough for insertion of intravenous therapy needle 18 and needle guard 14 in an opened position. In the preferred embodiment it is contemplated for top cover spring 16 and needle guard spring 12 to exert minimal forces, respectively, to extend top cover 6 upward and away from bottom cover 8 and to close needle guard 14 across the lower opening of bottom cover 8.

Figure 9:
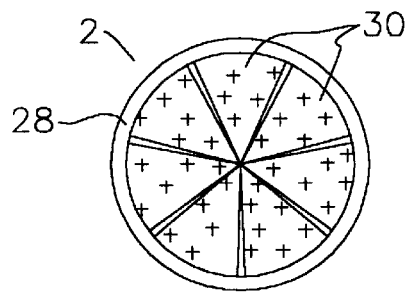
FIG. 9 is a bottom view of a second embodiment of the present invention having an outer cover and a collapsible needle guard attached to the outer cover and the needle guard in its collapsed position over the lower opening in the outer cover.
Figure 10:
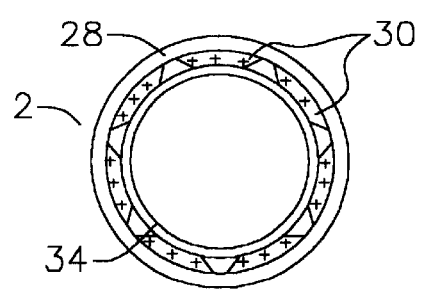
FIG. 10 is a bottom view of the second embodiment showing the present invention having an extendable inner cover, and a collapsible needle guard which is in its retracted position between the inner cover and the outer cover.
Figure 11:
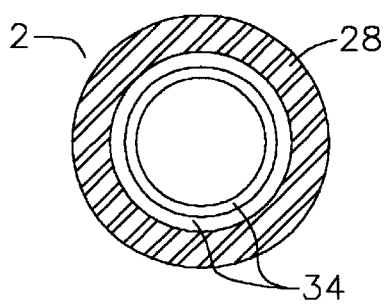
FIG. 11 is a top view of the second embodiment showing the present invention having an inner cove, an outer cover, and a quantity of flexible material attached across the upper opening in the inner cover.

FIG. 9 shows a second embodiment of needle cover invention 2 having an outer cover 28 and a collapsible needle guard 30 attached to the interior surface of outer cover 28. FIG. 9 shows collapsible needle guard 30 in its collapsed or needle tip guarding position across the lower opening of outer cover 28. FIGS. 10 and 11 show the second embodiment of needle cover invention 2 having an inner cover 34 which moves between a retracted position within outer cover 28 and an upwardly extended position beyond outer cover 28. FIG. 10 further shows collapsible needle guard 30 positioned between inner cover 34 and outer cover 28 when inner cover 34 is in its retracted position within outer cover 28. In the preferred embodiment, it is contemplated for inner cover 34, outer cover 28, and collapsible needle guard 30 to be made of puncture-resistant material. In the preferred embodiment, inner cover 34, outer cover 28 and collapsible needle guard 30 are made of plastic so that needle cover invention 2 may be disposable.

Figure 12:
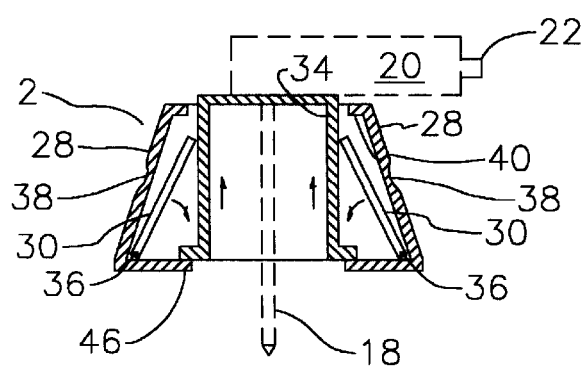
FIG. 12 is a side view of the second embodiment showing the present invention having a retracted inner cover and a collapsible needle guard which is in its retracted position.
Figure 13:
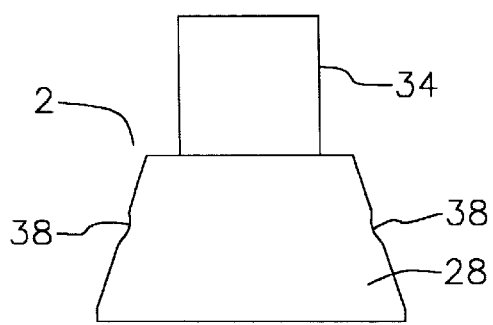
FIG. 13 is a side view of the second embodiment showing the present invention having an extended inner cover and finger grips on the outside surface of the outer cover to help keep the present invention positioned against a patient until the intravenous therapy needle is withdrawn from the adjacent port.
Figure 14:
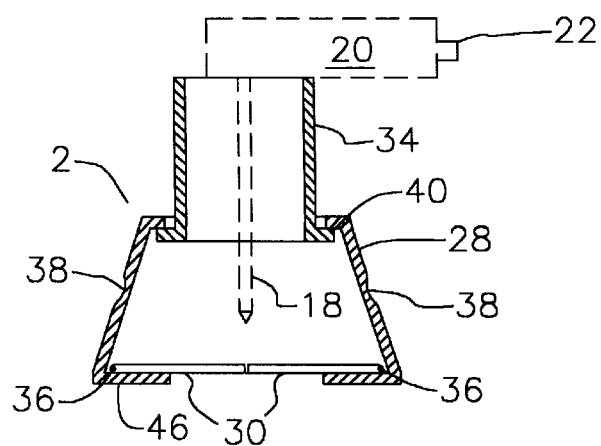
FIG. 14 is a side view of the second embodiment showing the present invention having an extended inner cover and a collapsible needle guard in its collapsed position over the lower opening in the outer cover.

FIGS. 12, 13 and 14 show the second embodiment of needle cover invention 2 having finger grips 38 on the outside surface of outer cover 28. FIGS. 12 and 14 shows collapsible needle guard 30 which is made of a plurality of generally triangular shaped portions, each, attached to the inside surface of outer cover 28 by outer cover hinges 36. A lip 46 around the inside bottom opening of outer cover 28 prevents inner cover 34 from moving downwardly beyond outer cover 28. Similarly, stopping means 40 prevent inner cover 34 from moving upwardly beyond the central top opening of outer cover 28. FIG. 12 shows inner cover 34 in a retracted position, while FIGS. 13 and 14 show inner cover 34 in its extended position. FIG. 12 depicts the normal relationship of outer cover 28 and the inner cover 34 before intravenous needle 18 is inserted or pushed into the patient.

In each of the previously described embodiments, intravenous needle 18 is typically held in place by the frictional attachment to the self-sealing septum of the ports of needle delivery systems or by the frictional attachment to the skin and veins of the patient. For example, it is known that when a needle or pin is penetrated into the skin, the needle will remain pricked into the skin until removed.

To use the first embodiment of needle cover invention 2, one inserts intravenous therapy needle 18 through slit 26 and into the area defined by extended top cover 6 and bottom cover 8. Needle support 20 is attached to needle clamp 4. Needle guard 14 is then placed in its opened position to expose the lower opening in bottom cover 8. As top cover 6 is made to retract into bottom cover 8, intravenous therapy needle 18 may be inserted into a subcutaneously implanted venous access port (not shown) positioned beneath needle cover invention 2. When intravenous therapy needle 18 is ready to be withdrawn from the port, top cover 6 extends through the upper opening in bottom cover 8 as intravenous therapy needle 18 is withdrawn so that top cover 6 and bottom cover 8 completely surround intravenous therapy needle 18 after withdrawal. Needle guard 14 then automatically closes over the lower opening in bottom cover 8 to protect the person withdrawing the needle from spattering blood and needle stick resulting from needle rebound.

To use the second embodiment of needle cover invention 2, inner cover 34 is retracted into outer cover 28 with collapsible needle guard 30 being positioned between inner cover 34 and outer cover 28. Intravenous therapy needle 18 is then made to extend through inner cover 34 and into a subcutaneously implanted port (not shown) positioned beneath needle cover invention 2. When intravenous therapy needle 18 is ready to be withdrawn from the port, the person withdrawing intravenous therapy needle 18 stabilizes outer cover 28 by holding finger grips 38, allowing inner cover 34 to extend through the upper opening in outer cover 28. Concurrent with the extension of inner cover 34 as shown by the upward directional arrows in FIG. 12, hinges 36 cause collapsible needle guard 30 to collapse into a position across the lower opening in outer cover 28. When intravenous therapy needle 18 is fully withdrawn, inner cover 34 is fully extended, and inner cover 34, outer cover 28 and collapsible needle guard 30 completely surround intravenous therapy needle 18.

What is claimed is:

1. A multi-piece cover for use over a central venous access port needle delivery system which is subcutaneously implanted into a patient and for use with intravenous therapy and other indwelling needle systems used to access the central venous access port, the multi-piece cover comprising:

a first cover member having a bottom opening and a central top opening at its top surface;

a second cover member having an upper surface opening and a lower surface opening, said second cover member being slidedly positioned within the first cover member so as to be in a generally collapsed position within the first cover member for initial needle insertion into the patient;

the second cover member further being slidedly extendable through said top opening in the first cover member for removal of the needle from the patient; and needle guarding means for the bottom opening of the first cover member, wherein when the second cover member is collapsed into first cover member, the needle guarding means is in an open position from the bottom opening to allow the needle to be inserted into the patient, and wherein when the needle is to be withdrawn from the patient, the second cover member is slidedly extended upwardly from the first cover member to maintain the needle within an area defined by the first cover member and the second cover member, and the needle guarding means is hingedly biased to a closed position across the bottom opening of the first cover member for protection during removal of the needle from spattering blood and needle stick resulting from needle rebound.

2. The multi-piece cover according to claim 1 wherein the upper opening in the second cover member comprises a needle accepting aperture slightly larger in diameter than said needle.

3. The multi-piece cover according to claim 1 wherein the needle guarding means comprises a needle guard hingedly attached to said first cover member and spring bias means for positioning the needle guard to the closed position across the bottom opening of the first cover member.

4. The multi-piece cover according to claim 1 further comprising stopping means for preventing the second cover member from extending upwardly beyond the central top opening of the first cover member.

5. The multi-piece cover according to claim 1 further comprising a needle clamp attached to the second cover member for securing a needle support portion of the needle against the second cover member upper surface during use.

6. The multi-piece cover according to claim 1 further comprising spring bias means to bias said second cover member into its extended position.

7. A multi-piece cover for use over a central venous access port needle delivery system which is subcutaneously implanted into a patient and for use with an intravenous therapy indwelling needle system used to access the central venous access port, the multi-piece cover comprising:

a first cover member having a bottom opening and a central top opening at its top surface;

a second cover member having an upper surface needle accepting aperture and a lower surface opening, said second cover member being slidedly positioned within said first cover member so as to be in a generally collapsed position within the first cover member for initial needle insertion into the patient;

the second cover member further being slidedly extendable through said top opening in the first cover member for removal of the needle from the patient; and needle guarding means for the bottom opening of the first cover member attached to said first cover member, wherein when the second cover member is collapsed into first cover member, the needle guarding means is in an open position from the bottom opening to allow the needle to be inserted through said upper surface needle accepting aperture into the patient, and wherein when the needle is to be withdrawn from the patient, the second cover member is slidedly extended upwardly from the first cover member to maintain the needle within an area defined by the first cover member and the second cover member, and the needle guarding means is hingedly biased to a closed position across the bottom opening of the first cover member for protection during removal of the needle from spattering blood and needle stick resulting from needle rebound.

8. The multi-piece cover according to claim 7 wherein the needle guarding means comprises a needle guard hingedly attached to said first cover member and spring bias means for positioning the needle guard to the closed position across the bottom opening of the first cover member.

9. The multi-piece cover according to claim 7 further comprising a needle clamp attached to the second cover member for securing a needle support portion of the needle against the second cover member upper surface during use.

10. The multi-piece cover according to claim 7 further comprising stopping means for preventing the second cover member from extending upwardly beyond the central top opening of the first cover member.

11. A multi-piece cover for use over a central venous access port needle delivery system which is subcutaneously implanted into a patient and for use with an intravenous therapy and other indwelling needle systems used to access the port, the multi-piece cover comprising:

a first cover member having a bottom opening and a central top opening at its top surface;

a second cover member having an upper surface opening and a lower surface opening, said second cover member being slidedly positioned within the first cover member so as to be in a generally collapsed position within the first cover member for initial needle insertion into the patient;

the second cover member further being slidedly extendable through said top opening in said first cover member for removal of the intravenous therapy needle from the patient;

the second cover member also having stopping means for preventing the second cover member from extending upwardly beyond the central top opening of the first cover member; and collapsible needle guarding means attached to said first cover member, the collapsible needle guarding means further including a plurality of generally triangular shaped portions, each portion being hingedly connected around an inside surface near the bottom opening of the first cover member, wherein when the second cover member is collapsed into first cover member for needle insertion into the patient through the lower surface opening of the second cover member, the needle guarding means is upwardly directed between the first cover member and the second cover member, and wherein when the second cover member is slidedly extended upwardly from the first cover member for withdrawal of the needle from the patient, the needle guarding means is biased downwardly clearing the stopping means to a closed position over the bottom opening of the first cover member so as to maintain the needle within an area defined by the first cover member, including the needle guarding means, and the second cover member for protection during removal of the needle from spattering blood and needle stick resulting from needle rebound.

12. The multi-piece cover according to claim 11 further comprising a lip about the inside bottom opening of the first cover member for maintaining the downwardly biased needle guarding means in the generally closed position over the bottom opening of the first cover member.

13. The multi-piece cover according to claim 12 further comprising finger grips in an outside surface of the first cover member.

* * * * *

UNITED STATES PATENT AND TRADEMARK OFFICE
CERTIFICATE OF CORRECTION

PATENT NO. : 6,238,375 B1  Page 1 of 1
DATED : May 29, 2001
INVENTOR(S) : Richard R. Powell It is certified that error appears in the above-identified patent and that said Letters Patent is hereby corrected as shown below:

Title page,
Item [54], replace Title with --RETRACTABLE COVER EXTRACTION DEVICE FOR INTRAVENOUS AND OTHER THERAPY NEEDLES --.

Column 1,
Line 7, replace "is not him limited" with -- is not limited --.

Column 2,
Line 42, replace "needle tip surrounds a" with -- surrounds a needle tip --.

Column 3,
Line 21, replace "automatically moves to close over the bottom opening in the cover" with -- acts as a barrier --.
Line 31, replace "collapsible cobling plastic" with -- collapsible folding plastic --.

Column 6,
Line 56, after "in outer cover 28" insert -- as shown by the directional arrows in Fig. 12 --.

Signed and Sealed this

Twenty-second Day of January, 2002

Attest:

*Attesting Officer*

JAMES E. ROGAN
*Director of the United States Patent and Trademark Office*